(12) United States Patent
Han et al.

(10) Patent No.: US 6,444,201 B1
(45) Date of Patent: *Sep. 3, 2002

(54) TREATMENT OF ALZHEIMER DISEASE BY MODULATION OF SYNAPSINS

(75) Inventors: Hui-Quan Han, Scotch Plains, NJ (US); Paul Greengard, New York, NY (US); Kenneth S. Kosik, Belmont; Adriana Ferreira, Boston, both of MA (US)

(73) Assignees: The Rockefeller University, New York, NY (US); Brighan and Women's Hospital, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/644,433

(22) Filed: May 13, 1996

Related U.S. Application Data

(63) Continuation-in-part of application No. 08/440,561, filed on May 12, 1995, now abandoned.

(51) Int. Cl.[7] .............................................. A61K 38/20
(52) U.S. Cl. ........................................ 424/85.2; 514/12
(58) Field of Search ...................... 514/12, 2; 424/85.1, 424/85.2

(56) References Cited

U.S. PATENT DOCUMENTS 5,571,893 A * 11/1996 Baker et al.
5,639,275 A * 6/1997 Baetge et al.
6,191,154 B1   2/2001 Landreth et al.

OTHER PUBLICATIONS

The Merck Manual of Diagnosis and Therapy (1992) 16th ed., ed. Robert Berkow, Merck Research Laboratories, Rathway, NJ, pp. 1403–1405, 2657.*
Lieberman, International Rev. of Neurobiol. 14 (1971) 49–124.*
Rudinger in "Peptide Hormones" (Jun. 1976) ed. J.A. Parsons, University Park Press, Baltimore, pp. 1–7.*
Jackowski. British J. of Neurosurgery 9 (1995)303–317.*
Olson Experimental Neurol. 124 (1993) 5–15.*
Cohen. Science 270(1995): 908.*
Ceccaldi et al (1995) J. Cell Biol. 128:905–12.
De Cruz e Silva et al (1995) Neuroprotocols 6 (proof copy from author).
Valtorta et al. (1995) Europ. J. Neurosci., 7:261–70.
Alford et al. (1994) J. Histochem.Cytochem., 42:283–7.
Ferreira et al. (1994) Science, 264:977–9.
Han et al. (1994) PNAS, 91:8557–61.
Samuel et al. (1994) Archives of Neurology, 51:772–8.
Zhan et al. (1994) Dementia, 5:79–87.
Lassmann et al. (1993) Ann. NY Acad. Sci., 695:59–64.
Greengard et al. (1993) Science, 259:780–5.
Masliah et al. (1993) Medical Hypothesis, 41:334–40.
Zhan et al. (1993) Acta Neuropathologica 86:259–64.
Lu et al. (1992) Neuron, 8:521–529.
Valtorta et al. (1992) J. Biol. Chem., 267:7195–8.
Han et al. (1991) Nature, 349:697–700.
Kelly (1991) Nature, 349:650–1.
De Camilli et al. (1990) Annu. Rev. Cell Biol., 6:433–60.
Jovanovic et al. (1996) Proc. Natl. Acad. Sci. USA 93:3679–83.

* cited by examiner

*Primary Examiner*—Gary L. Kunz
*Assistant Examiner*—Robert C. Hayes
(74) *Attorney, Agent, or Firm*—Klauber & Jackson

(57) ABSTRACT

The role of synapsin II in both the reformation and the maintenance of synaptic connections in cultured hippocampal neurons can be the basis of therapy for neurodegenerative disorder, particularly Alzheimer disease, which involve the disruption of synapses. When synapsin II expression in neurons is blocked by antisense synapsin II oligonucleotides, the ability of hippocampal neurons to reform as well as to maintain synapses is severely disrupted. Antisense suppression of synapsin II after axon formation but immediately before synaptogenesis prevents synapse formation. Suppression of synapsin II after synaptogenesis disrupts the majority of existing synapses. Re-expression of synapsin II in synapsin deficient neurons achieved after removing the antisense oligonucleotides leads to the re-establishment of synaptic connections, providing direct evidence that synapsin II is required for the maintenance and/or restoration of synapses. Thus, therapeutic methods based on the reformation and the maintenance of synapses, including delivery of the synapsin cDNAS or proteins into the patient's nervous system, use of the synapsin cDNAS to promote the synapse forming ability of cells for grafting, and use of agents that increase the expression of, enhancing the activity of, or mimic the activity of, the endogenous synapsins, can provide treatment of neurodegenerative disorders.

14 Claims, 13 Drawing Sheets

Figure 1A:
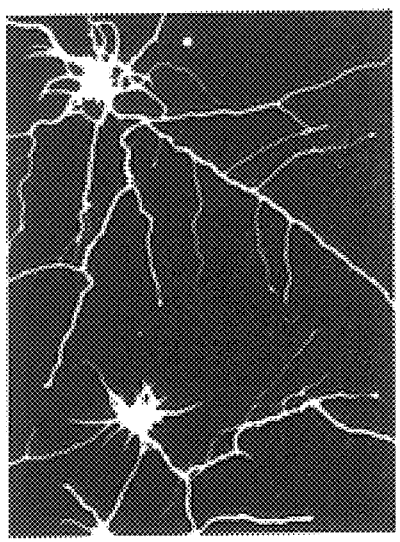

FIG.4A
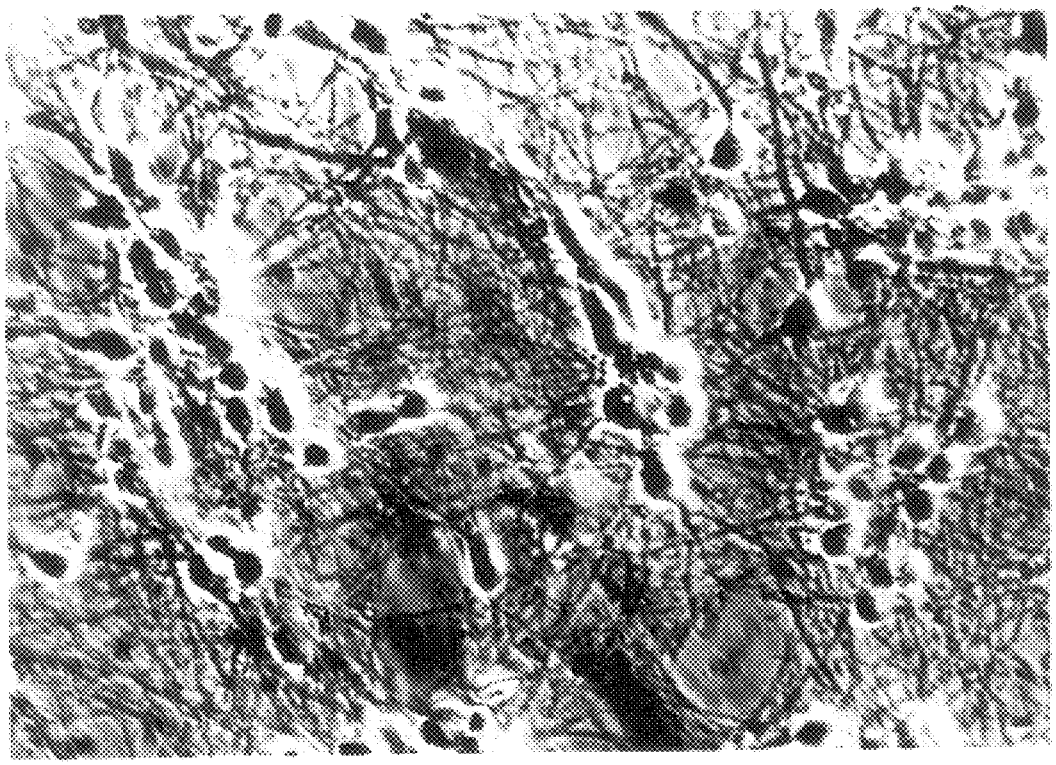
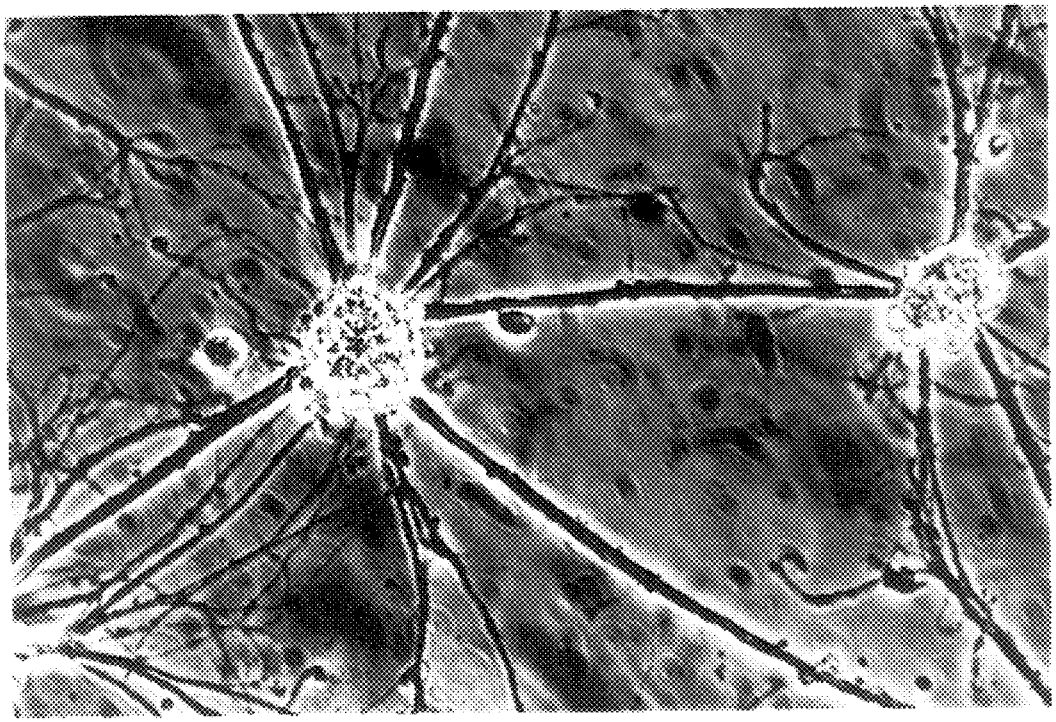
FIG.4B

FIG.6A
FIG.6B
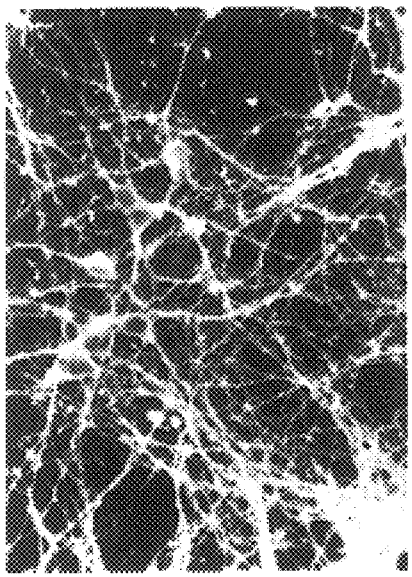
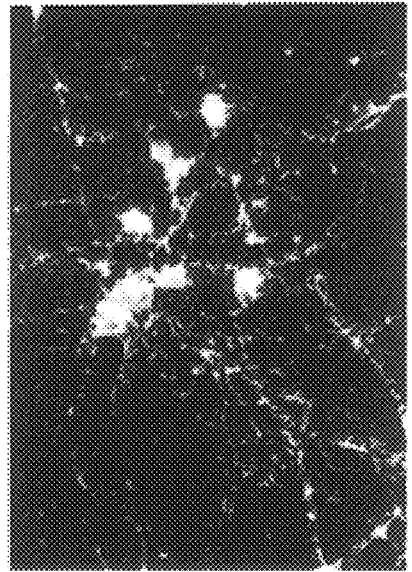
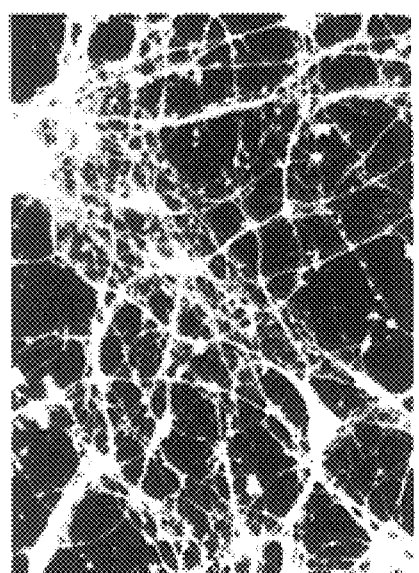
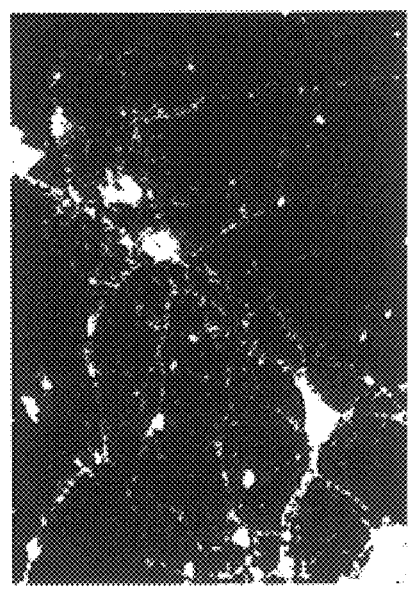
FIG.6C
FIG.6D

FIG.7A
FIG.7B
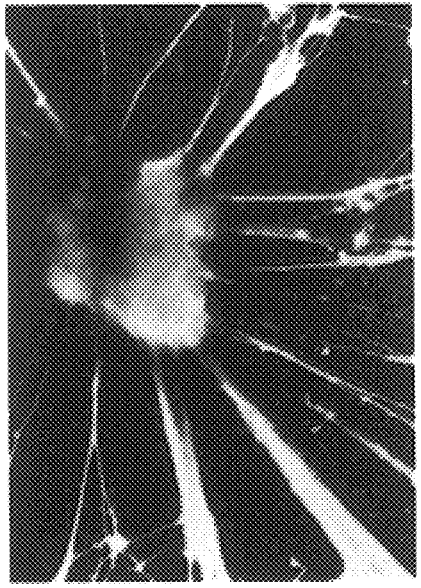
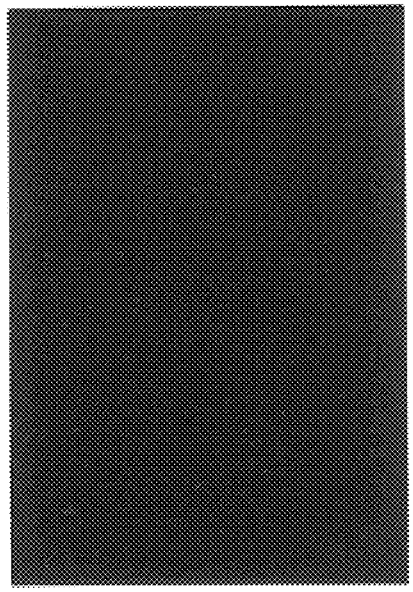
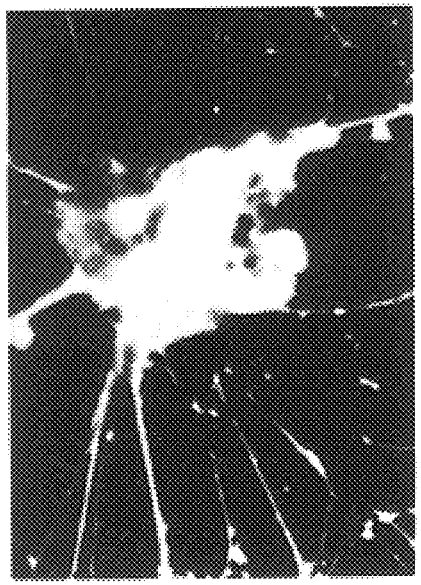
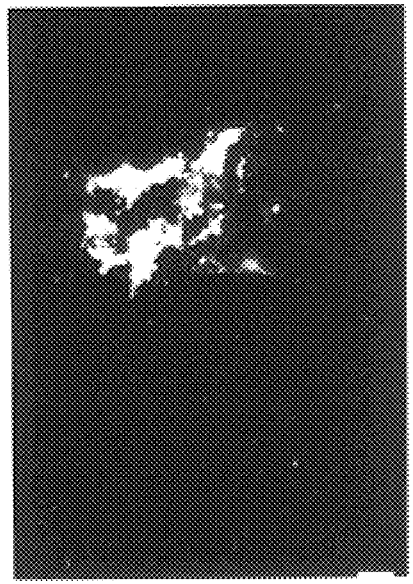
FIG.7C
FIG.7D

FIG.8A
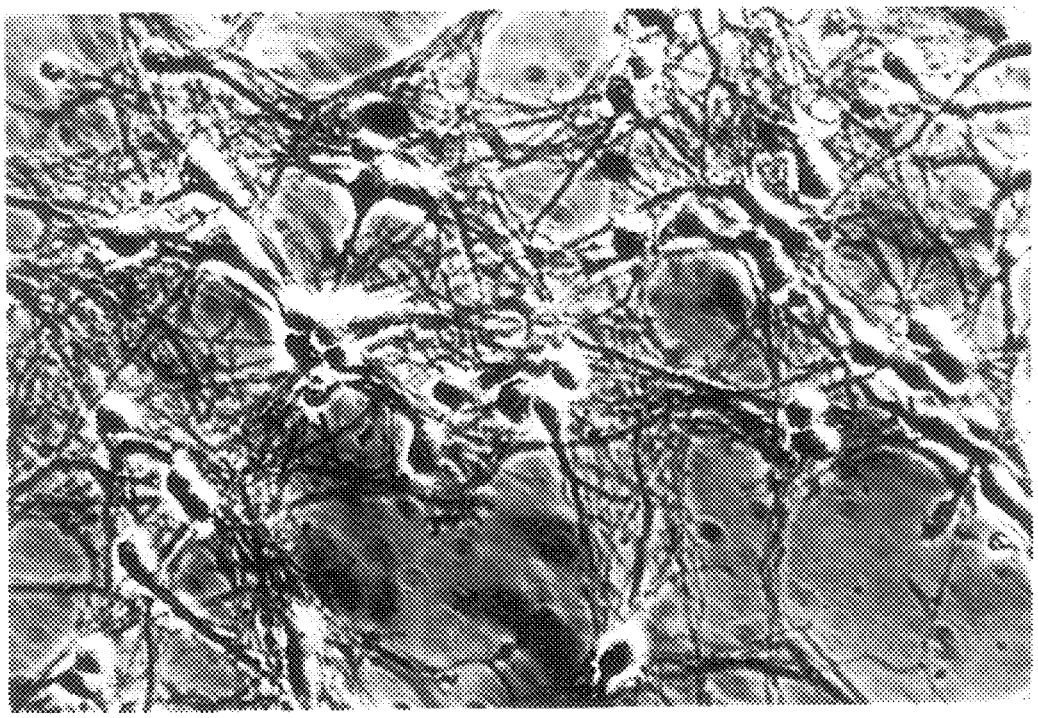
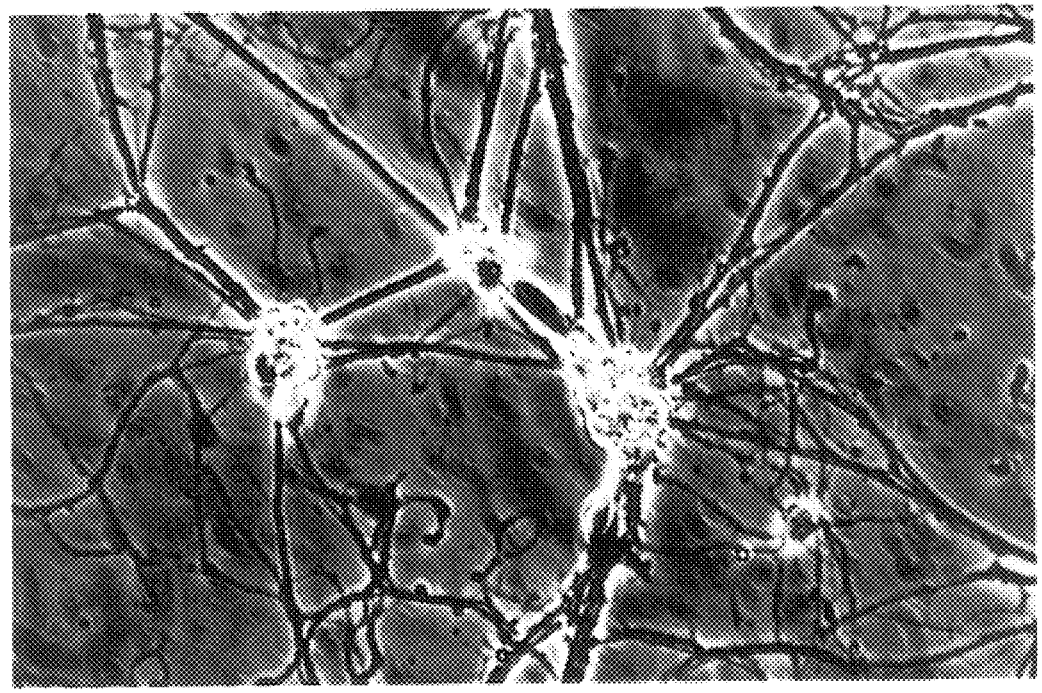
FIG.8B

TREATMENT OF ALZHEIMER DISEASE BY MODULATION OF SYNAPSINS

This application is a continuation-in-part of copending Application U.S. Ser. No. 08/440,561, filed May 12, 1995, now abandoned.

BACKGROUND OF THE INVENTION

Neurodegenerative diseases such as Alzheimer and Parkinson's diseases share a common pathological characteristic, i.e., the deterioration of nerve cell connections within the nervous system. As a consequence of the disruption of normal neuronal connections, patients suffer from a number of cognitive deficits including impaired learning and memory.

The central element of neuronal networks is the "synapse", which denotes the structural specialization of the junctional contact between two nerve cells. A synapse is a highly sophisticated electrochemical device composed of a presynaptic terminal and a specialized postsynaptic membrane. Only by establishing synaptic connections, can nerve cells organize into networks and acquire information processing capability such as learning and memory. Synapses are progressively reduced in number during normal aging, and are severely disrupted during neurodegenerative diseases, Alford, M. E. et al., J. Histochem. & Cytochem, 42:283–7 (1994), Lassmann, H. et al., Ann. NY Acad. Sci., 695:59–64 (1993), Zhan, S. S. et al, Acta Neuropathologica 86:259–264 (1993). Clinical dementia, the most common symptom of neurodegenerative diseases is best correlated with the severity of synaptic deterioration in the central nervous system, Samuel W. et al., Archives of Neurology, 51:772–8 (1994), Masliah, E et al., Medical Hypothesis, 41: 334–340 (1993), Zhan, S. S. et al., Dementia, 5: 79–97, (1994). Therefore, finding molecules capable of creating and/or maintaining synaptic connections is an important step in the treatment of neurodegenerative diseases.

During recent years, a great deal of effort has been made by investigators to characterize the function of synaptic proteins, i.e., proteins enriched in synapses. Examples of synaptic proteins with recently characterized functions are numerous, and include synaptotagmin, syntexin, synaptophysin, synaptobrevin, and the synapsins. In contrast to other synaptic proteins which are known to be involved in specific aspects of synaptic function, e.g., synaptic vesicle recycling or docking, the synapsins are now known to play a much broader organizational role in axonogenesis, in the differentiation of presynaptic terminals, and in the formation and maintenance of synaptic connections.

Synapsin I and synapsin II are a family of neuron-specific phosphoproteins which are highly concentrated in adult nerve terminals. Synapsin I and synapsin II are encoded by two genes, the synapsin I gene and the synapsin II gene. Alternative splicing of the primary transcripts of synapsins I and II genes gives rise to their protein products synapsins Ia and Ib and synapsin IIa and IIb which are collectively termed the synapsins. The four members of the synapsin family (synapsin Ia, Ib, IIa and IIb) share a high degree of homology in their cDNA and amino acid sequences. Domains A, B, C, are highly conserved common domains of the synapsin family and together occupy more than 80% of synapsin IIb, the shortest isoform of the family. Both synapsin I and II have been cloned and sequenced, Greengard et al., Science 259:780–785 (1993).

In mammals, the ontogeny of the synapsins coincides with the terminal differentiation of neurons, and the levels of expression of the synapsins parallel the formation of synapses in the nervous system. The synapsins exhibit a distinct pattern of distribution, being expressed only in the nervous system, present only in neurons but not in glial cells, and specifically localized in the presynaptic compartment of the synapses in adult nervous system where they are associated with the cytoplasmic surface of synaptic vesicles. In vitro binding analysis indicates that synapsins are able to interact with actin and other cytoskeletal elements in a phosphorylation dependent manner. Both synapsin I and synapsin II are able to bundle filamentous actin, and phosphorylation of synapsin by protein kinases leads to a reduction in actin-bundling capability. Transfection of synapsins, regardless of isoform, into fibroblast cells resulted in a remarkable reorganization of cytoskeleton and the formation of highly elongated cellular processes, Han & Greengard, PNAS, 91:8557–8561 (1994). Synapsins are also able to interact with synaptic vesicles in a phosphorylation-sensitive fashion. Both synapsin I and synapsin II are able to bind to the cytoplasmic surface, and the binding affinity of synapsin to synaptic vesicles is regulated by phosphorylation. Thus, the synapsins are capable of interacting with multiple macromolecular components within the nerve terminal. Currently, the effects of synapsins on the organization of actin cytoskeleton are thought to be a cell biological basis underlying synapsin's function in neuronal development, De Camilli, P. et al., Annu. Rev. Cell Biol. 6:433–460, (1990), Valtorta et al., J. Biol. Chem, 267:7195–7198 (1992) and Greengard et al., Science 259:780–785 (1993).

Synapsin I and synapsin II have been intensively analyzed for their role in the regulation of neurotransmitter release from adult nerve terminals. A large body of experimental evidence shows that the synapsins are important regulatory molecules that control synaptic release of neurotransmitters, Greengard et al., Science 259:780–785 (1993).

The first demonstration of synapsins effect on neuronal cell development came from a transfection experiment in which cDNA encoding synapsin IIb was introduced to a cell line NG108–15, Han, et al., Nature, 349:697–700 (1991). NG108–15 is a line of hybrid cells made by cell fusion between mouse neuroblastoma and rat glioma cells. When treated with agents that raise the intracellular cyclic AMP level, this cell line undergoes differentiation and becomes neuronal-like. When synapsin IIb was overexpressed by transfection, NG108–15 cells unexpectedly acquired a much stronger neuronal phenotype: having more neuritic varicosities (nerve terminals) per cell, more synaptic vesicles per varicosity, and more synaptic vesicle-associated proteins. Thus, synapsin IIb and possibly other synapsins (based on their high sequence homologies) are implicated in the formation of presynaptic terminals.

Subsequent studies performed in a totally different system, i.e., the frog embryos, provided further supportive evidence for the role of synapsins in nerve cell development. Injection of synapsin protein into early developing frog embryo (at several cell stage) caused the nerve cells (which came into being 24 hours after the injection into form synapses with muscle cells more effectively, Lu et al., Neuron 8:521–529 (1992).

These results suggested that the synapsins may play a role in synaptogenesis. However, the experimental approaches used in the above experiments were insufficient in establishing a clear relationship between synapsins and synaptogenesis due to the fact that the systems used did not involve a pure neuronal context. The NG108–15 cells are not real neurons and the results obtained need further verifications using real neurons. In the frog embryo experiment, synapsin was not directly injected into developing neuronal cells but rather into a several cell-stage embryo. Therefore there was a lack of direct evidence for the effects of synapsins obtained from a pure neuronal system.

The present invention relates to the discovery of the role of synapsin II in a pure neuronal system, and the concomitant utilities available for therapy from these discoveries.

OBJECTS OF THE INVENTION

It is an object of the present invention to provide a method of maintaining and/or restoring synapses in a patient in need of therapy for a neurodegenerative disorder by administration of an agent in an amount sufficient to maintain and/or restore synapses.

It is a further object of the present invention to provide a method of treatment for neurodegenerative disorders which comprises administration to a patient in need of such treatment an amount sufficient to maintain and/or restore synapses of a therapeutic agent capable of maintaining and/or restoring synapses.

It is a still further object of this invention to provide a method of maintaining and/or restoring synapses by the administration of the synapsin cDNAs or proteins into the patient's nervous system.

It is an object of the present invention to provide a method of maintaining and/or restoring synapses by administration of the synapsin cDNAS to promote the synapse forming ability of cells for grafting.

It is a further object of this invention to provide a method of maintaining and/or restoring synapses by the administration of an agent that increases the expression of, or enhances the activity of, the endogenous synapsins.

It is a still further object of the present invention to provide a method of treatment for Alzheimer disease by administration to a patient in need of such treatment an amount sufficient to maintain synapses of a therapeutic agent which mimics the activity of synapsin and is thus capable of maintaining and/or restoring synapses.

SUMMARY OF THE INVENTION

The present invention relates to a method of maintaining and/or restoring synapses in a patient in need of therapy for a neurodegenerative disorder by administration of an agent in an amount sufficient to maintain and/or restore synapses. More particularly, the present invention concerns a method of treatment for neurodegenerative disorders which comprises administration to a patient in need of such treatment an amount sufficient to maintain and/or restore synapses of a therapeutic agent capable of maintaining and/or restoring synapses.

BRIEF DESCRIPTION OF THE DRAWING FIGURES

Figure 1B:
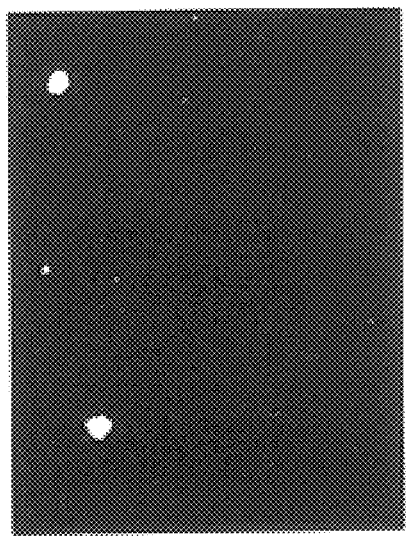

FIGS. 1A & 1B are photographs of the untreated hippocampal neurons at 3 days in culture which show the double immunofluorescence staining of a same field for tubulin (A) and synapsin II (B). Note that the hippocampal neurons at 3 days in culture have acquired highly branched axons and well-differentiated dendritic trees (A), and synapsin II was primarily localized in the cell body (B) as well as in axons.

Figure 1C:
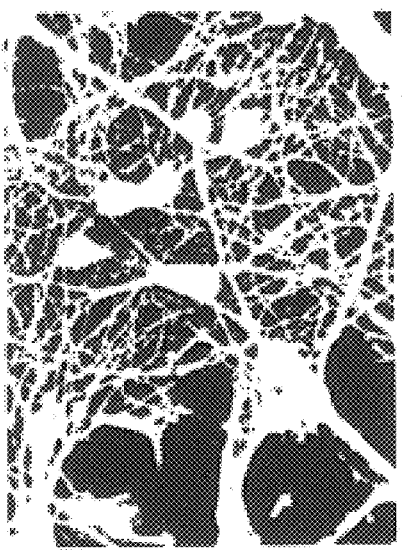
Figure 1D:
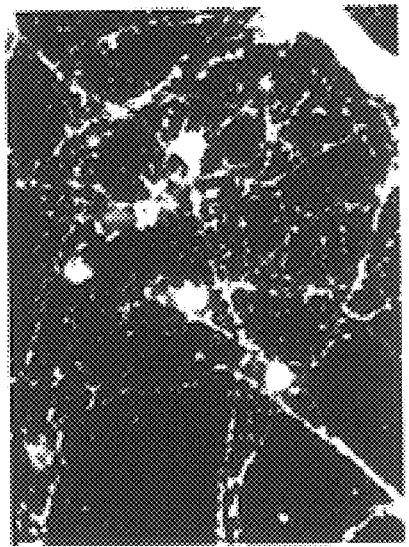

FIGS. 1C & 1D are photographs of the untreated hippocampal neurons at 8 days in culture which show the double immunofluorescence staining of a same field for tubulin (A) and synapsin II (B). Note that at 8 days in culture, the neurites of hippocampal neurons have made extensive network connections (A) and synapsin II has translocated into the synapses shown as large punctate staining at the nerve cell connections.

Figure 2A:
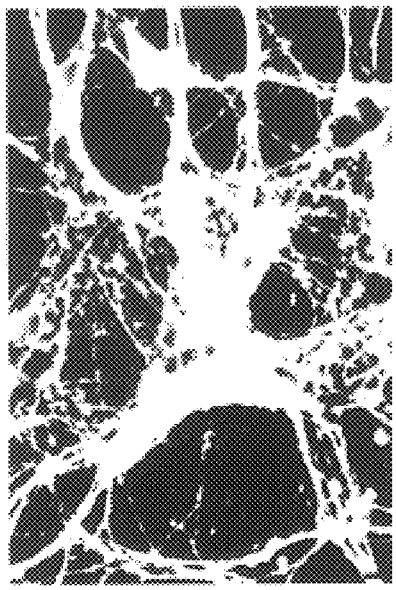
Figure 2B:
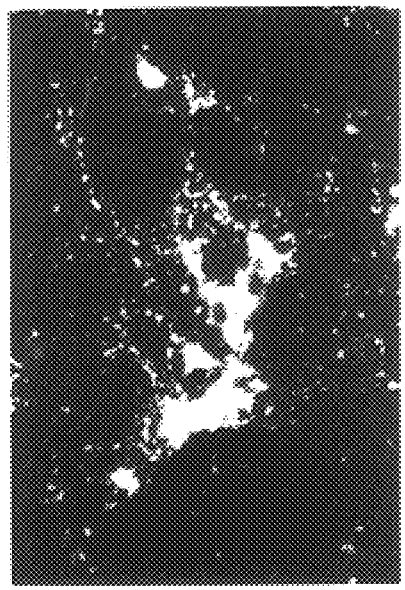

FIGS. 2A & 2B are photographs showing hippocampal neurons at 8 days in culture which had been treated with sense synapsin II oligonucleotide for five days (Day 3–Day 8). The hippocampal neurons were double stained for tubulin (A) and synapsin II (B). Note that the sense-treatment did affect the synapsin II expression and had no effect on the neuronal connections.

Figure 2C:
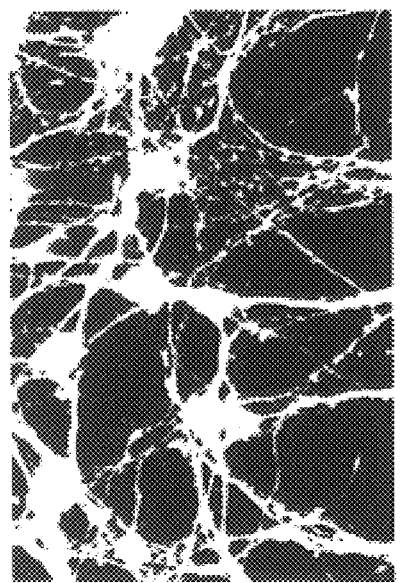
Figure 2D:

FIGS. 2C & 2D are photographs showing hippocampal neurons at 8 days in culture which have been treated with sense synapsin II oligonucleotide for five days (Day 3–Day 8). The hippocampal neurons were double stained for tubulin (A) and synaptophysin, a marker for synapses (B).

Note that in sense-treated neurons, numerous synapses were detectable as synaptophysin punctates that were associated with neurite connections.

Figure 3A:
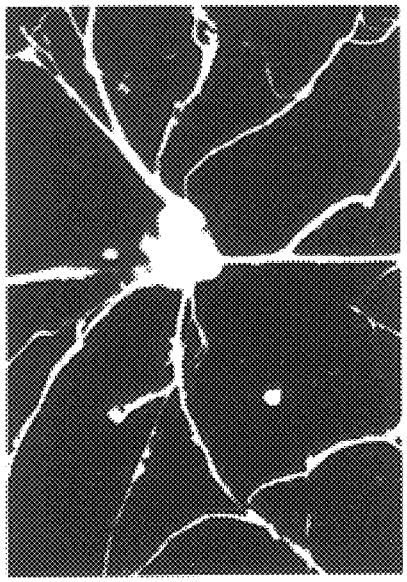
Figure 3B:
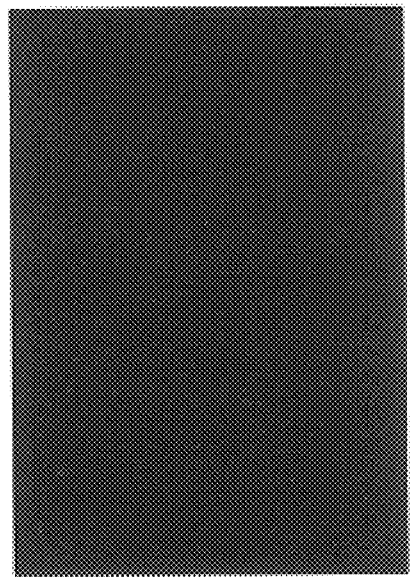
Figure 3C:
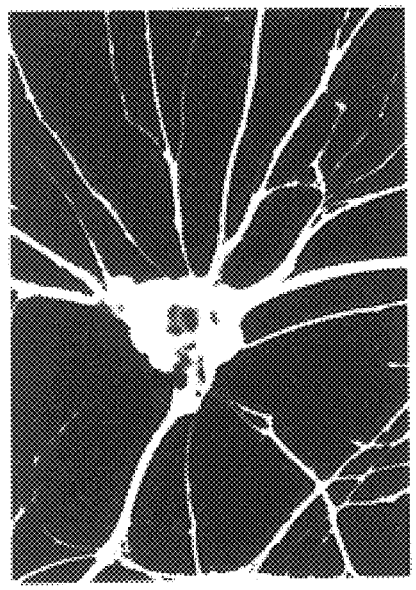
Figure 3D:
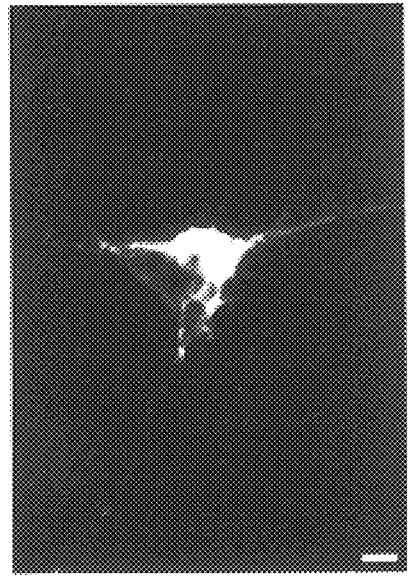

FIGS. 3A & 3B are photographs showing hippocampal neurons at 8 days in culture which have been treated with antisense synapsin II oligonucleotide for five days (Day 3–Day 8). The hippocampal neurons were double stained for tubulin (A) and synapsin II (B). Note that synapsin II immunoreactivity was no longer detectable after antisense-treatment (B), and associated with the depletion of synapsin II, there was a dramatic alteration in cell morphology as shown in A (Compare FIG. 3A with FIGS. 1C & 2C). FIGS. 3C & 3D are photographs showing hippocampal neurons at 8 days in culture which have been treated with antisense synapsin II oligonucleotide for five days (Day 3–Day 8). The hippocampal neurons were double stained for tubulin (A) and synaptophysin (B). Note that synaptophysin punctates were no longer existing in neurites, indicating the lack of synaptic connections.

FIGS. 4A & 4B are light microscopic images of hippocampal cultures at 8 days in culture which had been treated with sense synapsin II oligonucleotide (A) or with antisense synapsin II oligonucleotide (B) for 5 days (Day 3–Day 8). Note the neuritic fasciculation and clustering of cell bodies in B.

Figure 5A:
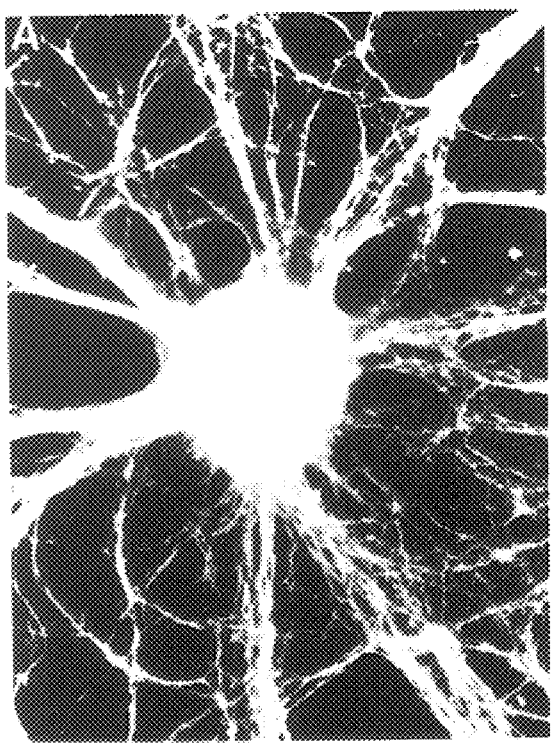
Figure 5B:
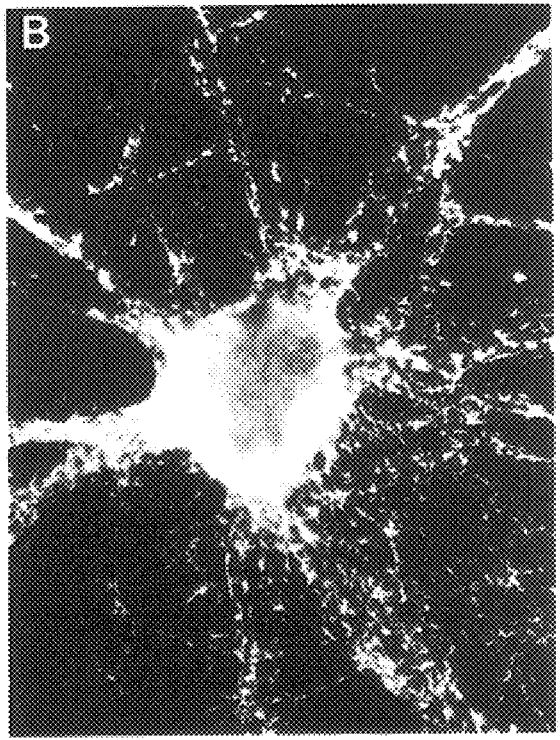

FIGS. 5A & 5B are photographs showing the double immunofluorescence staining for synapsin II (B) and tubulin (A) in a culture which was allowed to recover for days in the absence of oligonucleotide after having been treated with antisense synapsin II oligonucleotide for 5 days (Day 3–Day 8). Note the reappearance of strong synapsin II immunoreactivity in B, and associated recovery in cell morphology in A.

Figure 5C:
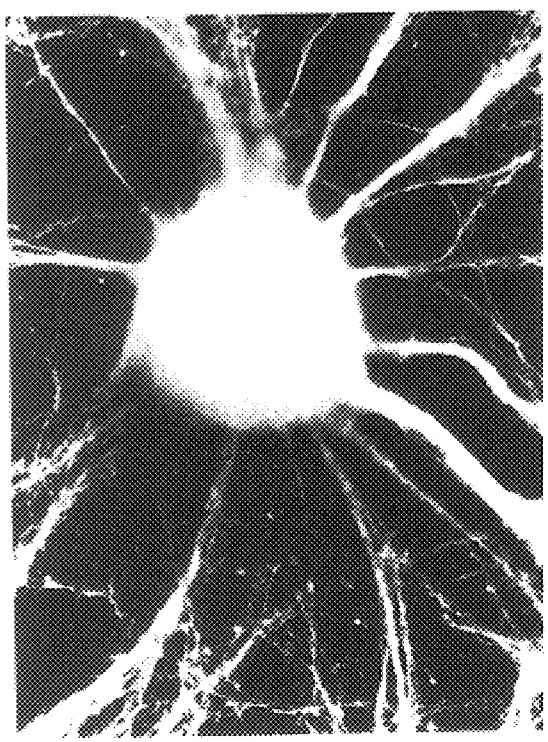
Figure 5D:
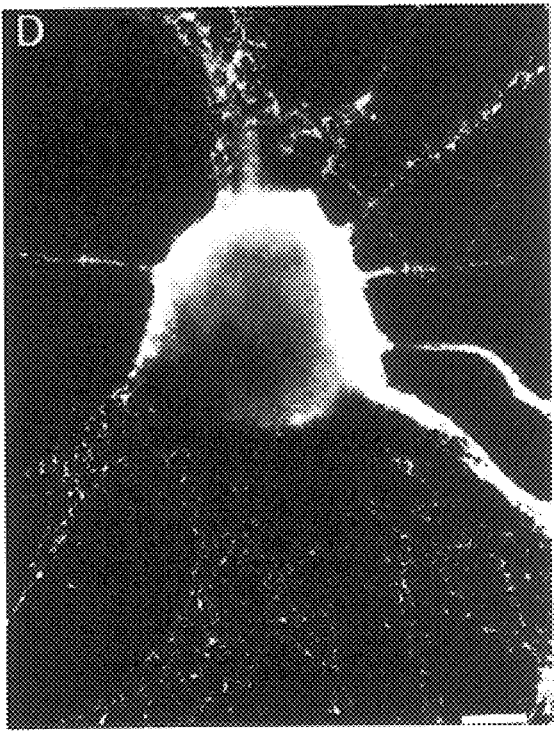

FIGS. 5C & 5D are photographs showing the double immunofluorescence staining for synaptophysin (D) and tubulin (C) in a culture which was allowed to recover for 10 days in the absence of oligonucleotide after having been treated with antisense synapsin II oligonucleotide for 5 days (Day 3–Day 8). Note in D that strong synaptophysin punctate staining reappeared in neurites, indicating the re-establishment of synaptic connections.

FIGS. 6A & 6B are photographs showing hippocampal neurons at 15 days in culture which had been treated with sense synapsin II oligonucleotide for five days (Day 10–Day 15). The hippocampal neurons were double stained for tubulin (A) and synapsin II (B). Note that the sense-treatment did affect the synapsin II expression and had no effect on the neuronal connections.

FIGS. 6C & 6D are photographs showing hippocampal neurons at 15 days in culture which have been treated with sense synapsin II oligonucleotide for five days (Day 10–Day 15). The hippocampal neurons were double stained for tubulin (A) and synaptophysin (B). Note that in sense-treated neurons, numerous synapses were detectable as the punctate staining for synaptophysin that were associated with neurite connections.

FIGS. 7A & 7B are photographs showing hippocampal neurons at 15 days in culture which had been treated with antisense synapsin II oligonucleotide for five days (Day 10–Day 15). The hippocampal neurons were double stained for tubulin (A) and synapsin II (B). Note that synapsin II immunoreactivity was no longer detectable after antisense-treatment (B), and associated with the depletion of synapsin II, there was a dramatic alteration in cell morphology as shown in A (Compare FIG. 7A with FIGS. 6A & 6C).

FIGS. 7C & 7D are photographs showing hippocampal neurons at 15 days in culture which had been treated with antisense synapsin II oligonucleotide for five days (Day 10–Day 15). The hippocampal neurons were double stained for tubulin (A) and synaptophysin (B). Note that synaptophysin punctates were no longer existing in neurites, indicating the lack of synaptic connections.

FIGS. 8A & 8B are light microscopic images of hippocampal cultures at 15 days in culture which had been treated with sense synapsin II oligonucleotide (A) or with antisense synapsin II oligonucleotide (B) (Day 10–Day 15). Note the neuritic fasciculation and clustering of cell bodies in B.

Figure 9A:
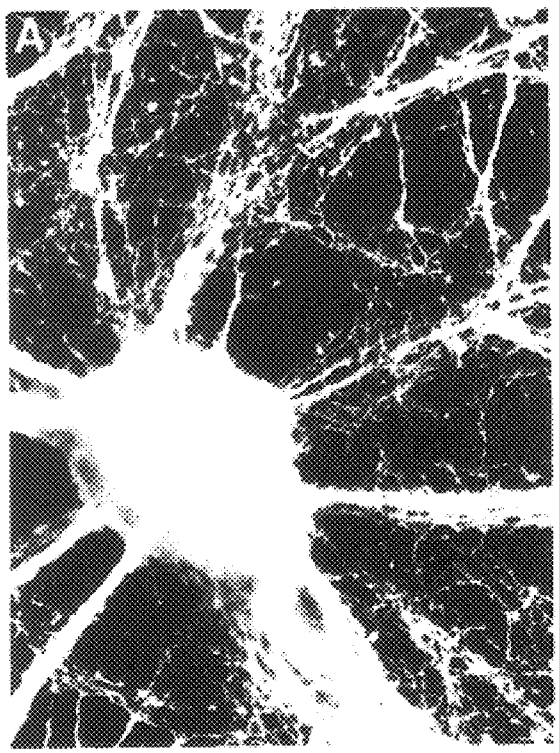
Figure 9B:
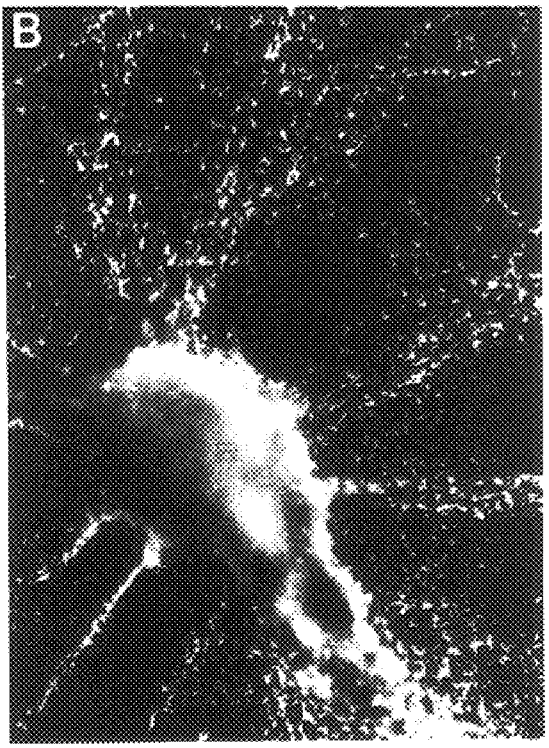

FIGS. 9A & 9B are photographs showing the double immunofluorescence staining for synapsin II (B) and tubulin (A) in a culture which was allowed to recover for 10 days in the absence of oligonucleotide after having been treated with antisense synapsin II oligonucleotide for 5 days (Day 10–Day 15). Note the reappearance of strong synapsin II immunoreactivity in B, and associated recovery in cell morphology in A.

Figure 9C:
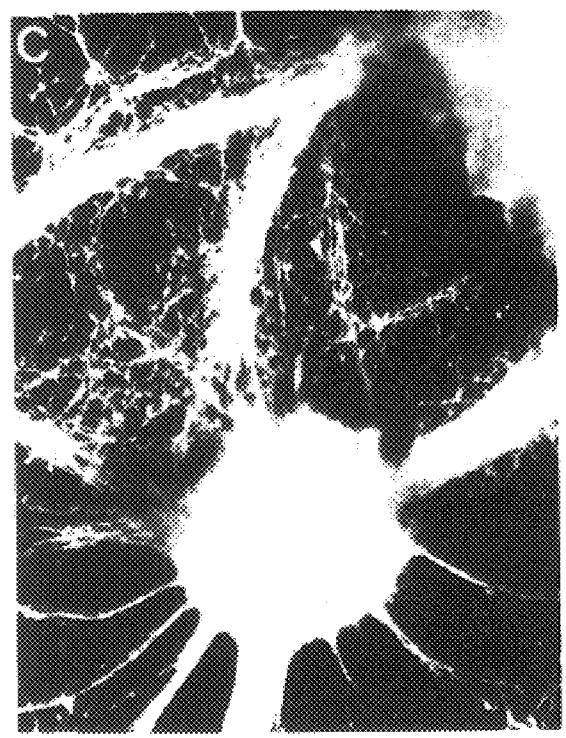
Figure 9D:
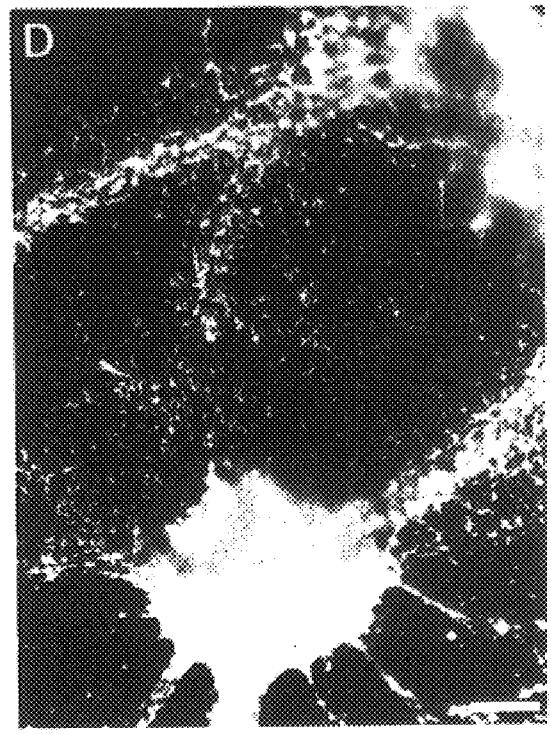

FIGS. 9C & 9D are photographs showing the double immunofluorescence staining for synaptophysin (D) and tubulin (C) in a culture which was allowed to recover for 10 days in the absence of oligonucleotide after having been treated with antisense synapsin II oligonucleotide for 5 days (Day 10–Day 15). Note in D that strong synaptophysin punctate staining reappeared in neurites, indicating the re-establishment of synaptic connections.

Figure 10A:
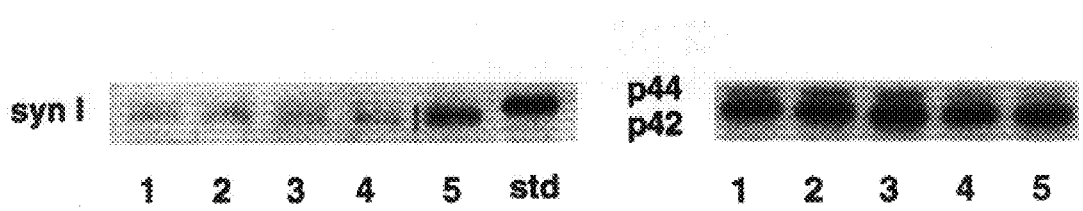
Figure 10B:
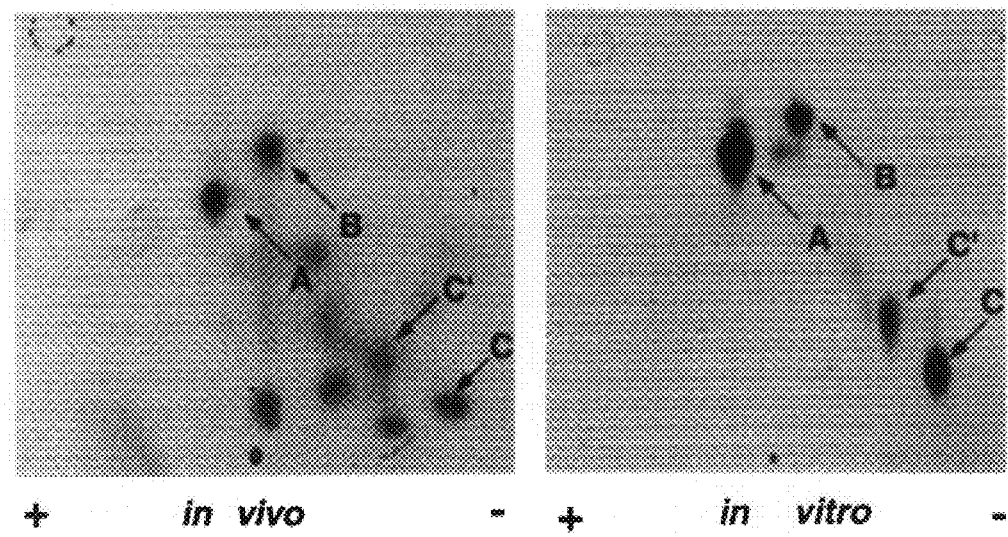

FIGS. 10A–B are immunoblots which show (A) immunoblot analysis of the distribution of MAP kinase phosphorylated synapsin 1 using P-site 4/5 Ab (left) and MAP kinase isoforms, p44 and p42 (right), in subcellular fractions of rat brain, SDS extracts (40 μg) of homogenate (lane 1), S1 (lane 2), 52 (lane 3), P2 (lane 4), and purified synaprosomes (lane 5) were subjected to SDS-PAGE. Bovine phosphosynapsin 1 standard (std; 100 ng/lane) migrates with a slightly higher apparent molecular mass than the rat isoform. (b) Two-dimensional phosphopeptide maps of $^{32}$p-labeled synapsin I phosphorylated in purified synaptosomes (left) and in vitro by MAP kinase (right). Phosphopeptide A corresponded to HPLC peak 2 (residues 54–73); phosphopeptide B corresponded to HPLC peak 1B (residues 54–76); phosphopeptide C corresponded to HPLC peak 1A (residues 533–544); phosphopeptide C was a cyclized form of phosphopeptide C, with a pyroglutamyl residue at the N terminus.

Figure 11A:
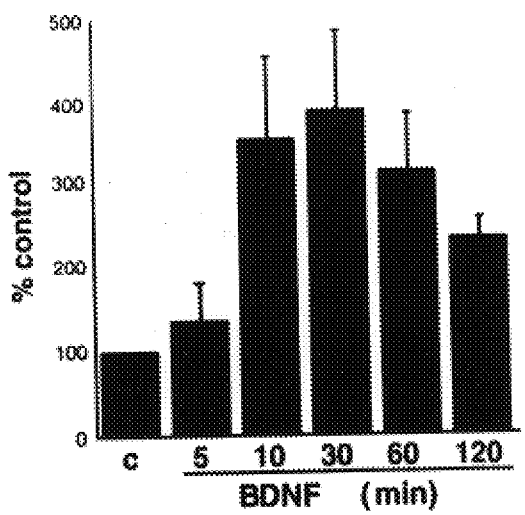
Figure 11B:
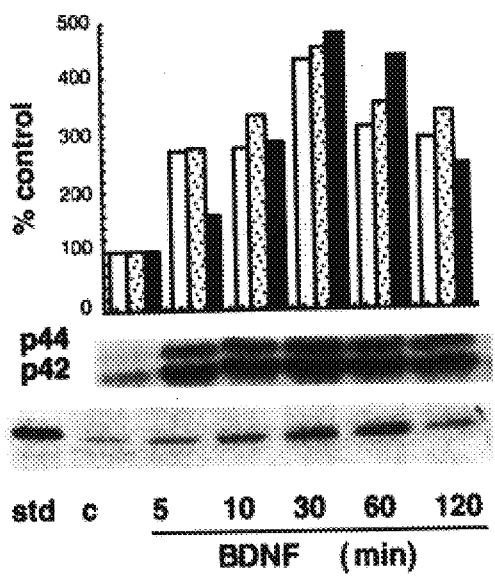
Figure 11C:
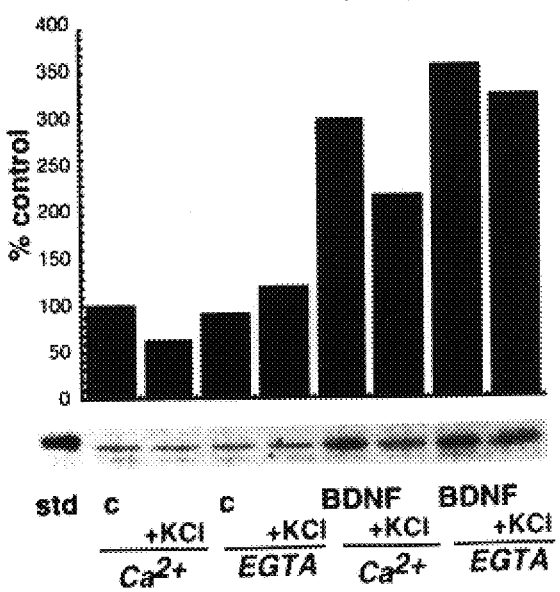
Figure 12:
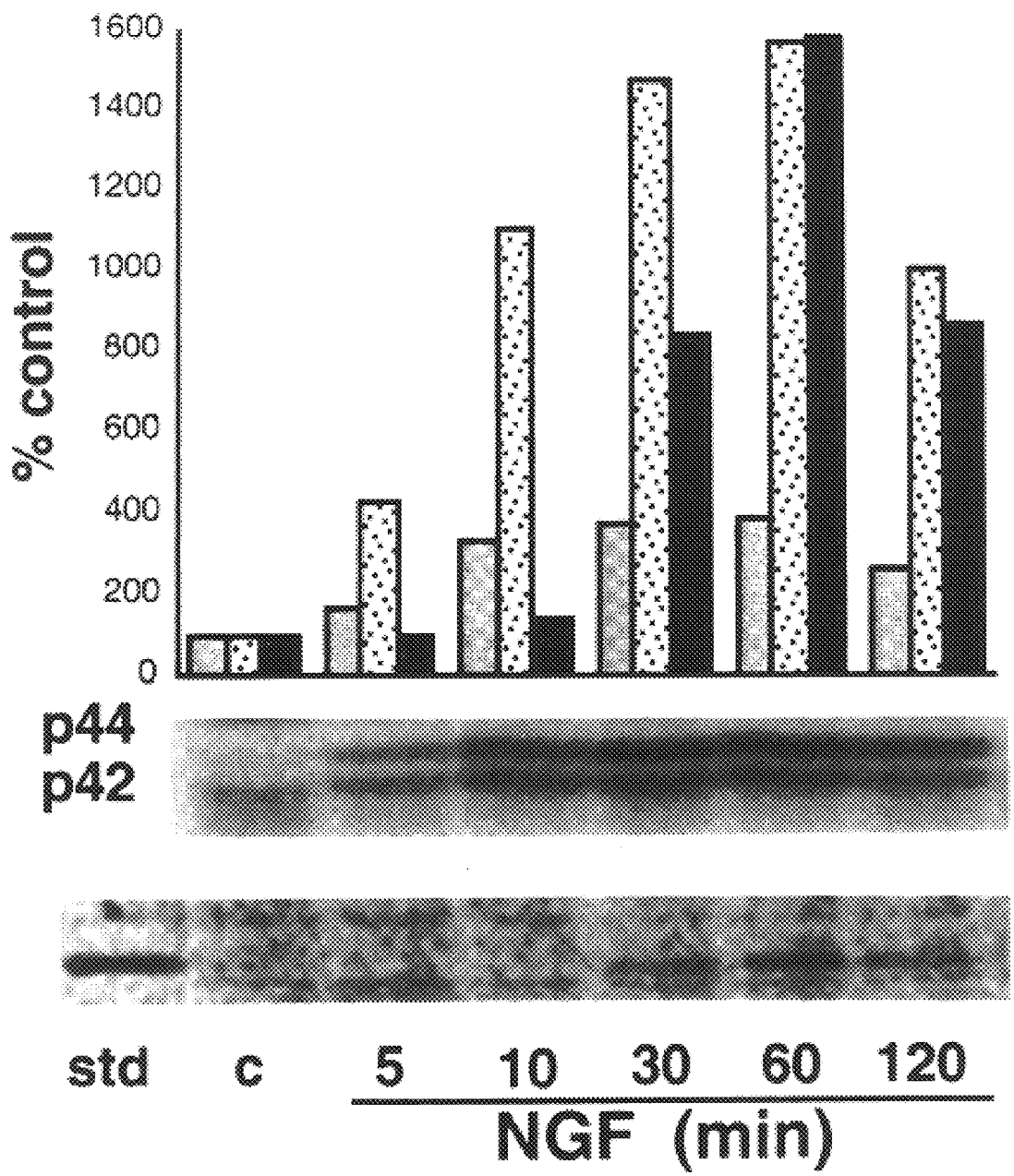

FIGS. 11A–C are graphs illustrating the comparison of (A) Effect of BDNF (50ng/ml) on the phosphorylation of synapsin I at sites 4/5 in cerebrocortical neurons (n=4). (B) Top comparison of effects of BDNF on activation of the MAP kinase isoforms p42 (■) and p44 (□) and phosphorylation of synapsin I at sites 4/5 (■). Middle Autoradiogram of in-gel MAP kinase assay. Bottom Immunoblot analysis of synapsin I phosphorylation using P-site 4/5 Ab. Results are representative of four independent experiments. (C) $Ca^{2+}$-dependent dephosphorylation of synapsin I at sites 4/5. Cultures of cerebrocortical neurons were incubated in the absence (lanes c) or presence (lanes BDNF) of BDNF for 20 minutes in the presence of 1mM extracellular $Ca^{2+}$ (lanes $Ca^{2+}$) or $Ca^{2+}$-free medium containing 0.2 mM EGTA (lanes EGTA). Where indicated, samples were depolarized using 60 mM KCl for 1 minute (lanes +KCl). FIG. 12 is a graph showing the effect of NGF (50 ng/ml) on the phosphorylation of synapsin I at sites 4/5 in PC12 cells. (Top) Comparison of effects of NGF on activation of the MAP kinase isoforms p42 (■) and p44 (□) and phosphorylation of synapsin I at sites 4/5 (■). (Middle) Autoradiogram of in-gel MAP kinase assay. (Bottom) Immunoblot analysis of synapsin I phosphorylation using P-site 4/5 Ab. Results are representative of three independent experiments.

Figure 13A:
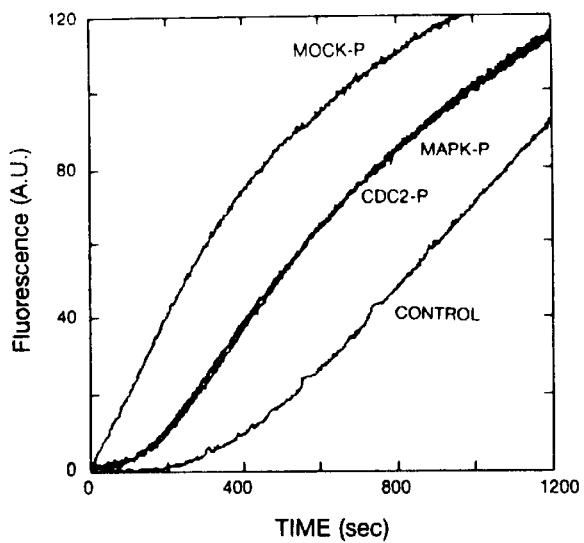
Figure 13B:
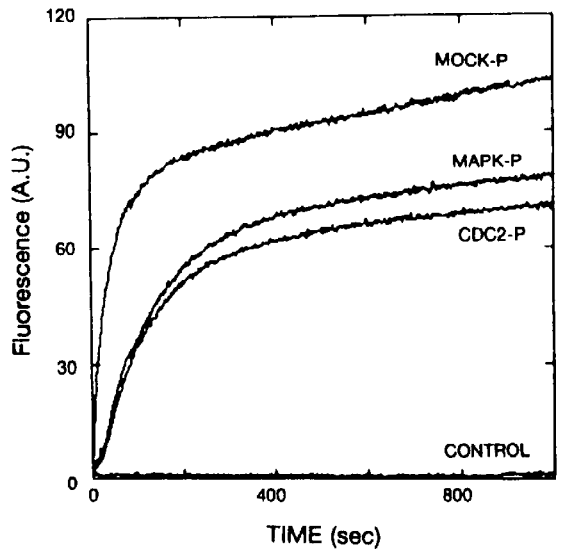
Figure 13C:
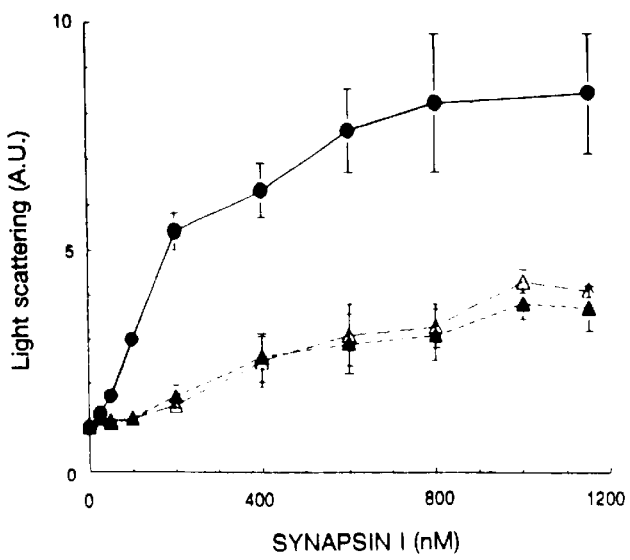

FIGS. 13A–C are graphs showing the ability of various phosphorylated forms of synapsin I to nucleate and polymerize G-actin and bundle F-actin. The synapsin I preparations used were: synapsin I storage buffer alone (CONTROL trace), 300 nM mock-phosphorylated synapsin I (MOCK-P trace). 300 nM synapsin I phosphorylated by MAP kinase (sites 4, 5, and 6) (MAPK-P trace), or 300 nM synapsin I phosphorylated by edk (site 6) (CDC2-γ trace), (A) Effect of site-specific phosphorylation on the synapsin I-induced acceleration of G-actin polymerization. Polymerization of pyrenyl-G-actin was triggered at a time 0 by the addition of KCL and $M_2Cl_2$ in the presence of the indicated phosphorylated form of synapsin I. Polymerization of pyrenyl-G-actin was analyzed by measuring the fluorescence increase associated with the G-actin-F-actin transition. Experiments were performed under conditions of low ionic strength as earlier described. (H) Effect of site-specific phosphorylation on synapsin I-induced actin nucleation and polymerization. The polymerization of pyrenyl-G-actin as triggered by the addition nat time 0 of the indicated phosphorylated form of synapsin I in the absence of KCl and $MgCl_3$. Experiments were performed under conditions of high ionic strength. (C) Effects of site-specific phosphorylation on synapsin I-induced F-actin bundle formation. F-actin as incubated with the indicated phosphorylated forms of synapsin I (●; MOCK-P; Δ; MAPK-P; ▲; CDC2-P) for 30 minutes at room temperature, and the extent of filament bundling was measured by light scattering. No bundling was seen in the absence of synapsin I. A, U, arbitrary units).

DETAILED DESCRIPTION OF THE INVENTION

The present invention concerns a method of treatment for neurodegenerative disorders which comprises administration to a patient in need of such treatment an amount sufficient to maintain and/or restore synapses of a therapeutic agent capable of maintaining and/or restoring synapses.

As shown by the experimental details which follow, the maintenance and/or restoration of synapses can effect therapeutic benefits in the treatment of neuro-degenerative disease wherein the manifestations of the disease result in incomplete neurotransmission, thus resulting in an improvement and/or reversal of the deterioration of the nervous system of the patient under treatment. By "restoration of synapses" is meant the regeneration or reformation and refunctionalization of synapses after nerve cells have ceased to exhibit normal synapses, as a result of a neurodegenerative disease.

Numerous neurodegenerative diseases affect humans, particularly the elderly, and result in an enormous cost both economically and socially to society. Among such diseases, Alzheimer disease is perhaps the most pervasive, but others such as senile dementia, Pick's disease and Parkinson's disease are also the result of the degeneration of the nervous system.

Using a pure neuronal system, i.e., primary hippocampal neurons in culture, the instant invention has been able to establish the critical role of synapsin proteins, and especially synapsin II, in synaptogenesis and particularly in synapse maintenance and restoration. Administration of synapsin II antisense oligonucleotides to cultured hippocampal neurons at different stages of development results in the suppression of the expression of synapsin II. Further examination has focused on the consequences of synapsin II depletion on neuronal development with special reference to neurite outgrowth, neuronal morphology and synaptic density.

In the therapeutic method of the present invention, an agent is administered in an amount sufficient to maintain and/or restore synapses to the patient under treatment. Several agents can be utilized to accomplish this method. In a first embodiment of the present invention, the agent can be a synapsin cDNA or protein, or an active fragment thereof, which is administered into the patient's nervous system to effect the desired synapsin maintenance and/or restoration. Both synapsin cDNA and synapsin proteins have been isolated, and methods for their preparation are known in the art.

In a second embodiment of the present invention, the agent is a synapsin cDNA which is administered to cells for grafting to promote their synapse forming ability In a third embodiment of the present invention, an agent is administered which modulates and/or regulates, i.e., increases the expression of, or enhances the activity of, the endogenous synapsins in the nervous system of the patient under treatment. The following is a list of agents which can be utilized in the present invention to increase the expression, or enhance the activity, of the endogenous synapsins in the nervous system of a patient under treatment.
1. Trophic factors and cytokines such as NGF (nerve growth factor), EGF (epidermal growth factor), BDNF (brain derived neurotrophic factor), NT-3 (neurotropin-3), NT-4 (neurotropin factor), CNTF (cilliary neurotrophic factor), IL-6 (interleukin-6), and active fragments thereof, etc.
2. cyclic adenosine 3', 5'-monophosphate (cAMP) and derivatives.
3. Nicotines, and other cholinergic agonists.
4. Estrogen, thyroid hormone, and natural and synthetic derivatives thereof.

This listing is not meant to be a complete or exhaustive list, but is representative of the modulators useful in the methods of the present invention.

In a still further embodiment of the present invention, an agent is administered which mimics the activity of the natural synapsin proteins in the nervous system of the patient under treatment. Such agents may be synthetic preparations based on natural synapsins, i.e., active fragments of the protein, or may be small molecules which otherwise do not resemble the natural proteins, but which are capable of effecting their function.

The active agents for use in the present invention can be, and are preferably, administered as a medicament, i.e., a pharmaceutical composition.

The pharmaceutical compositions used in the methods of this invention for administration to animals and humans comprise an active agent in combination with a pharmaceutical carrier or excipient.

The medicament can be in the form of tablets (including lozenges and granules), dragees, capsules, pills, ampoules or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or, for example, a half, a third or a quarter of a daily dose will depend on whether the medicament is to be administered once, or, for example, twice three times or four times a day, respectively.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The active agent can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active agent can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90%. of the active ingredient by weight of the total composition.

In addition to the active agents, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active agent will be administered perorally, parenterally (for example, intramuscularly, intraperitoneally, subcutaneously, transdermally or intravenously), rectally or locally, preferably orally or parenterally, especially perlingually, or intravenously.

The dosage rate, e.g., 0.05 to 20 mg/kg of body weight, will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

EXAMPLES

Example 1

In the instant studies, three different developmental time windows of hippocampal neurons were studied: 1. Axon formation (within 24 hours of plating), 2. Synapse formation (3 days-8 days in culture), and 3. maintenance of formed synapses (10 days-15 days in culture).
1. Axon Formation This work has been published in the May 13 1994 issue of Science (Ferreira et al., Science, 1994). Twenty-four hours after plating, hippocampal neurons quickly put out axon and minor cellular processes. Within this twenty-four hour period, it was determined whether synapsin II expression is required for the establishment of normal neurites by inhibiting synapsin II expression with antisense oligonucleotides to synapsin II. The results indicate that hippocampal neurons that are depleted of synapsin II lost their ability to grow normal neurites including axons and dendrites and appear to be grossly aberrant in their morphology. In addition, depletion of synapsin II resulted in a selective decrease in a number of synaptic proteins including synapsin I, synaptophysin, synaptotagmin and syntexin.

Corroborative evidence for the role of synapsin in neurite outgrowth was obtained from recent transfection experiments. These experiments showed that when synapsin I and II were transfected into non-neuronal cells (fibroblast cells and endocrine cells), there was a remarkable change in cell morphology characterized by outgrowth of highly elongated and branched cellular processes as well as by a drastic slow-down in cell division. These results were published in the August 1994 issue of PNAS (Han & Greengard, PNAS, 1994).
2. Synaptogenesis At 3 days in culture, the hippocampal neurons become more mature with their minor processes differentiating into dendritic trees and their axons becoming more branched (FIG. 1A). At this stage, synapsin II was primarily localized in the cell body as well as in the axons (FIG. 1B). Synaptogenesis takes place around 5 days in culture. By 8 days in culture, numerous synapses with typical mature synaptic ultrastructural characteristics are well-established (data not shown) and synapsin II become highly concentrated in synapses (FIG. 1D) where it was found to be colocalized with other synaptic vesicle proteins such as synaptophysin (data not shown). Thereafter, the density of synapses in culture remains relatively constant for several weeks (Dotti et al., J. Neurosci. 8 (1988); Fletcher, T. L. et al., J. Neurosci. 11 (1991)). To examine the role of synapsin II in synaptogenesis, hippocampal neurons were treated with either sense or antisense synapsin II oligonucleotide beginning at 3 days in culture. To rule out possible non-specific effect, two non-overlapping sense or antisense synapsin II oligonucleotides were used and the exact sequences have been reported in the Science paper published May 13, 1994. Immunostaining of synapsin II revealed that synapsin II level was significantly reduced to background level after two days of treatment (data not shown), and was virtually undetectable after 5 days of treatment (FIG. 3B), with either of the two non-overlapping antisense oligonucleotides. In contrast, synapsin II level was not affected after 5 day treatment with sense synapsin II oligonuleotides (FIG. 2B). After 5 days of treatment with antisense oligonucleotides, cultures were analyzed (at 8 days in culture) for their synaptic density by synaptophysin staining (FIG. 3D). As compared to untreated or sense-treated controls (FIG. 2D), antisense-treated cultures exhibited a drastic reduction in the number of immunoreactive spots for synaptophysin (FIG. 3D, Table 1 below) and synapsin I (Table 1), markers for synapses (Dotti et al., J. Neurosci. 8 (1988); Fletcher T. L. et al., J. Neurosci. 11 (1991)). This indicates that neurons with established axons and dendrites failed to form synaptic connections as a result of synapsin II depletion. In addition, synapsin II-depleted cultures showed a marked alteration in cell morphology that was characterized by fasciculation of neurites and clustering of cell bodies (FIG. 4B), whereas sense-treatment did not produce any alteration in cell morphology (FIG. 4A). Further testing was conducted to determine whether the inability to form synapses and the abnormal cell morphology of antisense-treated hippocampal neurons may be reversed after removing the antisense synapsin II from cultures to allow re-expression of synapsin II. Seven days after removal of the antisense oligonucleotides, strong synapsin II immunoreactivity reappeared in neurons which was associated with a remarkable recovery of synaptic density as revealed by staining with antibodies against synaptophysin or synapsin I (Table 1). By 10 days after removal of antisense oligonucleotides, both the synaptic density and the cell morphology recovered towards the control level (FIG. 5). These results provide strong evidence that synapsin II expression is necessary for synapse formation in neurons and further indicate that synapsin II re-expression can restore normal synaptic density and neuronal morphology in grossly aberrant synapsin II-deficient neurons. Reference to the figures provides a detailed description of the results.

3. Maintenance of Synapses

Finding molecules that are important for maintaining or stabilizing established synaptic connections is one of the most important issues in neuroscience. These experiments were conducted to determine whether synapsin II is also be involved in the maintenance of established synapses. Synapsin II sense or antisense oligonucleotides were administered to hippocampal cultures beginning at 10 days in culture after onset of synaptogenesis. After 5 days of treatment with sense or antisense synapsin II oligonucleotides, hippocampal neurons were analyzed for synaptic density at 15 days in culture. Five day treatment with synapsin II sense oligonucleotides did not affect either the synapsin II level (FIG. 6B) or the synaptic density (FIG. 6D). In contrast, 5 day treatment with synapsin II antisense oligonucleotides led to a depletion of synapsin II (FIG. 7B). Staining of synaptophysin (FIG. 7D, Table 1 below) and synapsin I (Table 1 below) revealed that the majority of immunoreactive spots for both of these synaptic markers disappeared, indicating a loss of most the existing synapses. Furthermore, associated with the synapsin II depletion, there was an alteration in cell morphology featuring neurite fasciculation and clustering of cell bodies (FIG. 8B). In contrast, synapsin II sense oligonucleotides did not produce any significant change in either the density of synaptophysin and synapsin I immunoreactive spots or in cell morphology (FIG. 8A). Removal of the antisense synapsin II oligonucleotides from the cultures led to synapsin II re-expression (FIG. 9B) in the synapsin II-deficient neurons and the reappearance of synaptophysin (FIG. 9D) and synapsin I immunoreactive spots (Table 1 below). Seven days after the removal of the antisense oligonucleotides, the synaptic density (the number of synaptophysin and synapsin I immunoreactive spots) was recovered completely (Table 1 below). Ten days after antisense removal, the cell morphology was largely back to normal (FIG. 9). These results demonstrate for the first time that synapsin II plays a critical role in the maintenance of the established synaptic connections.

TABLE I

Effect of synapsin II suppression on the number of synapses present in E18 hippocampal neurons grown in culture

| Days in culture | Synaptic marker | Pretreatment | Treatment None | Sense (−13 + 10) | Antisense (−13 + 10) | Recovery (one week) |
|---|---|---|---|---|---|---|
| 3 | Synatophysin | 0 | | | | |
| 3 | Synapsin I | 0 | | | | |
| 8 | Synaptophysin | | 224 ± 15 | 220 ± 17 | 33 ± 3 | |
| 8 | Synapsin I | | 250 ± 18 | 230 ± 21 | 29 ± 3 | |
| 15 | Synaptophysin | | | | | 139 ± 20* |
| 15 | Synapsin I | | | | | 142 ± 12* |
| 10 | Synaptophysin | 250 ± 20 | | | | |
| 10 | Synapsin I | 263 ± 17 | | | | |
| 15 | Synaptophysin | | 275 ± 13 | 261 ± 14 | 78 ± 11* | |
| 15 | Synapsin I | | 289 ± 15 | 269 ± 15 | 65 ± 6* | |
| 22 | Synaptophysin | | | | | 320 ± 34* |
| 22 | Synapsin I | | | | | 356 ± 45* |

Twenty fields were analyzed for each experimental condition. Each number the mean ± S.E.
*p < 0.001

Example 2

Materials and Methods

In vitro Phosphorylation of Synapsin I by MAP Kinase and Identification of MAP Kinase-Dependent Phosphorylation Sites. Synapsin I was purified from rat and bovine brain as earlier described. MAP kinase, p44$^{mpk}$, and the cyclin-dependent protein kinase (cdkl)-cyclin A complex were purified from sea star oocytes and assayed as earlier described by using 50 μM [γ-$^{32}$P] ATP (DuPont/NEN) and 5 μM synapsin I. For stoichiometric phosphorylation, reactions were carried out for 2 hours with 7 μM synapsin I in the absence (MOCK-P) or presence of the indicted protein kinase. Samples were subjected to SDS/PAGE, followed by staining with Coomassie blue. Incorporation of $^{32}$P was quantitated by using a PhosphorImager (Molecular Dynamics). Two-dimensional phosphopeptide map analysis and phosphoamino acid analysis and in-gel MAP kinase assays were performed as earlier described. For sequence determination, rat synapsin I (340 μg) was stoichiometrically phosphorylated with p44$^{mpk}$ in the presence of trace amounts of [γ-$^{32}$P]ATP and digested for 36 hours at 37° C. in a buffer containing 100 mM Tris (pH 8), 10% (vol/vol) CH$_3$CN, 1% hydrogenated Triton X-100, and 17 μg each of trypsin and chymotrypsin; 1 M urea was added after 18 hours, $^{32}$P-labeled phosphopeptides were purified in a two-step procedure by reversed-phase HPLC using a C$_{18}$ column (0.46×15 cm, Vydac, Hesperia, Calif.). Two major $^{32}$P-labeled peaks were isolated by linear gradient elution in the first chromatographic step [buffer 1:10 mM potassium phosphate [pH 2.2] with an increasing concentration of 40% CH$_3$CN/20% isopropanol] Peaks 1 and 2 were further processed with a different buffer system (buffer 2:0.1% trifluoroacetic acid with increasing concentrations of 70% CH$_3$CN). Peak 1 was resolved into two $^{32}$P-labeled phosphopeptides (peaks 1A and 1B), which appeared to be pure on the basis of absorbance profiles at 214 nm. Peak 2 was eluted as a single $^{32}$P-labeled peak in the second step. Each phosphopeptide was derivatized with ethanethiol prior to automated Edman degradation. The sequence obtained for peak 1A corresponded to residues 533–554 of rat synapsin I, with phosphoserine at residue 549: peak 1B corresponded to residues 54–76, with phosphoserine at residues 62 and 67; peak 2 corresponded to residues 54–73, with phosphoserine at residues 62 and 67.

Production of Phosphorylation State-Specific Antibodies and Immunoblot Analysis. Phosphorylation state-specific antibodies for the MAP kinase-dependent phosphorylation sites in synapsin I were products as earlier described. A peptide corresponding to residues 58–72 of synapsin I was chemically phosphorylated at residues Ser-62 and Ser-67 (referred to as P-sites 4 and 5, respectively) and was employed to generate rabbit polyclonal antibodies that specifically detected phosphorylation at these sites (P-site 4/5 Ab; G-526). A phosphopeptide corresponding to residues 545–555 of rat synapsin I was synthesized with phosphoserine at residues 549 (referred to as P-site 6) and used to generate antibodies that specifically detected phosphorylation at site 6 (P-site 6 Ab; G-555). Antisera were screened by immunoblot analysis with purified samples (100 ng) of dephospho-synapsin I, synapsin I phosphorylated by MAP kinase, and synapsin I phosphorylated at sites 1, 2, and 3 by PKA plus CaM kinase II. Each antibody was specific for MAP kinase-phosphorylated synapsin. The specificity of the P-site 4/5 Ab and P-site 6 Ab for their particular sites was confirmed by V8 protease digestion of MAP kinase-phosphorylated synapsin I, which generated an N-terminal fragment containing sites 4 and 5 and a C-terminal fragment containing site 6. Immunoblot analysis was carried out by using P-site 4/5 Ab and P-site 6 Ab (1:100 dilution), or anti-ERK1-antibody (1:500 dilution; K-23, Santa Cruz Biotechnology), followed by $^{125}$I-labeled anti-rabbit IgG (Amersham). In FIGS. 6–12, lanes containing purified bovine synapsin I phosphorylate by MAP kinase (100 ng) are indicated by "std". Lanes containing control samples [no treatment with brain-derived neurotrophic factor (BDNF) or nerve growth factor (NGF) are indicated by "c". Quantification of immunoblots was accomplished with a PhosphorImager.

Preparation and $^{32}$P-Prelabeling of Synaptosomes.

Synaptosomes from rat cerebral cortex were purified and prelabeled with $^{32}$Pi (Dupont/NEN) at 1 mCi/ml (1 Ci=37 GBq as earlier described. $^{32}$-labeled synapsin I was immunoprecipitated and subjected to SDS/PAGE and two-dimensional phosphopeptide map analysis.

Cell Culture. Embryonic day 18 rat cerebrocortical tissue was used to prepare primary neuronal cultures as earlier described. Cultures were maintained in serum-free medium for 5 days and then analyzed. PC12 cells were grown and maintained as earlier described. Hu-recombinant BDNF was supplied by Regeneron, and NGF (2.58) was purchased from GIBCO/BRI.

Actin Bundling and Polymerization Assays. Purification of actin, derivatization with N-(1-pyrenyl)iodoacetamide, and fluorescence measurements of polymerization were done as earlier described. Actin bundling was analyzed by light scattering assays and electron microscopy as described earlier.

RESULTS

Synapsin I Is Phosphorylated by MAP Kinase at Three Sites in Vitro. In vitro, synapsin I was found to be an excellent substrate for sea star MAP kinase. p44$^{mPk}$. Under initial rate conditions for synapsin I phosphorylation, non-linear double reciprocal plots were obtained. However, an estimate of $KO_{0.5}$ of synapsin I for MAP kinase was in the range of 20–50 μm, and the rate was comparable to that observed for myelin basic protein in assays run in parallel.

The stoichiometry of phosphorylation reached a maximal level of 3 mol of phosphate per mole of synapsin I. Phosphorylation of synapsin I by MAP kinase caused a reduction in electrophoretic mobility, which was not seen when synapsin I was phosphorylated at site 1 by PKA and/or at sites 2 and 3 by CAM kinase II or at site δ only by EDK1. Phosphoamino acid analysis demonstrated that only seryl residues were phosphorylated. Phosphopeptide map analysis of synapsin I phosphorylated by MAP kinase revealed a specific pattern of phosphopeptides (see FIG. 10B), which was distinct from those determined previously for other protein kinases. Protein microsequencing of purified phosphopeptides revealed two sites. Ser-62 and Ser-67 (referred to as sites 4 and 5, respectively), in the N-terminal "head" region of synapsin I. The third site, Ser-549 (referred to as site σ) was located in the C-terminal "tail" region of the molecule. Site 6 corresponded to the homologous site in bovine synapsin I (Ser-551) shown to by phosphorylated in vitro by the cdc2-cyclin A complex.

Synapsin I is Phosphorylated at MAP Kinase Specific Sites in Intact Preparations. Phosphorylation of synapsin I at sites 4/5 was detected under basal conditions in adult rat cerebral cortex homogenate, and this level appeared to become enriched in purified cerebrocortical synaptosomes (FIG. 10A, Left). Two major MAP kinase isoforms, p44 and p42, were present in various subcellular fractions, including presynaptic terminals (FIG. 10A Right). Basal phosphorylation of synapsin I at sites 4, 5 and 6 in synaptosomes was confirmed by immuno-precipitation of $^{32}$P-orthophosphate. The pattern obtained from two-dimensional phosphopeptide maps revealed nine phosphopeptides (FIG. 10B, Left) four of which corresponded to the phosphopeptides observed upon in vitro phosphorylation of synapsin I by MAP kinase (FIG. 10B Right).

MAP Kinase-Specific Phosphorylations of Synapsin I Is Regulated by Neurotrophins and Kcl-Depolarization. The regulation of synapsin I phosphorylation by MAP kinase was examined by primary cultures of rat cerebrocortical neurons. Synapsin I was phosphorylated at sites 4/5 under basal conditions, and this phosphorylation was increased by BDNF (FIG. 11A). The effect of BDNF was observed within 5 minutes, reached a peak of 3.87±1-fold (n-4) above control levels 30 minutes after addition and remained elevated over a 2-hour time period. Maximal stimulation of MAP kinase-specific phosphorylation of synapsin 1 by BDNF was observed at 50 ng/ml. BDNF-activated MAP kinase isoforms, p42 and p44, with a time course similar to that observed for synapsin I phosphorylation (FIG. 11B).

Depolarization of cerebrocortical neurons by 60 mM Kcl resulted in a Ca-$^{21}$ dependent decrease in the phosphorylation state of synapsin I at sites 4/5 (FIG. 11C) and site 6. Similar effects were observed with synaptosomes.

In PC12 cells, which express the Trk A receptor, the phosphorylation of synapsin I at sites 4/5 was low under basal conditions. NGF at 50 Ng/mi activated the two MAP kinase isoforms as well as the MAP kinase-specific phosphorylation of synapsin I (FIG. 12). In a previous study of PC12 cells. NGF was observed to stimulate phosphorylation of synapsin I at a novel site(s). On the basis of a comparison of the pattern obtained from two-dimensional phosphopeptide maps, together with the characteristic shift in the electrophoretic mobility of synapsin I, it is now possible to identify the previously unknown protein kinase responsible for the NGF-dependent phosphorylation of synapsin I in PC12 cells as MAP kinase.

Functional Properties of Synapsin I Are Regulated by MAP Kinase-Dependent Phosphorylation. In vitro, dephospho-synapsin I promotes the polymerization of G-actin and bundles actin filaments. The addition of dephospho-synapsin I immediately prior to nucleating salts abolishes the lag phase of polymerization (corresponding to the activation and nucleation of actin monomers), and in the absence of nucleating salts, induces polymerization. Both effects of synapsin I are reduced by phosphorylation at site I and abolished by phosphorylation at sites 2 and 3. Dose-response curves for the actin-bundling activities of mock-phosphorylated synapsin I and synapsin I stoichiometrically phosphorylated by either MAP kinase or cdkl were generated by using a light scattering assay. In comparison with the mock-phospho form of synapsin I, the MAP kinase-phospho form and the cdkl-phospho-form exhibited significantly reduced activity (FIG. 13C). The level of light scattering was reduced by a bout 50% at all concentrations tested, without any significant change in the apparent $ED_{50}$ for bundling. Electron microscopy data were consistent with these results.

In contrast to phosphorylation at sites 2 and 3, phosphorylation of synapsin I at sites 4, 5, and 6 or at site 6 alone did not significantly affect binding to purified synaptic vesicles.

DISCUSSION

Activation of MAP kinase in response to neurotrophic factors is believed to be critical for differentiation and survival of various neuronal populations. Neurotrophins have also been shown to have acute effects on synaptic transmission. The developmental effects of the neurotrophins involve transcriptional regulation, while the underlying basis for their effects on synaptic transmission may involve both presynaptic and postsynaptic mechanisms. These data provide evidence that synapsin I is a physiological substrate for MAP kinase and indicate that alteration of the actin-based cytoskeleton through MAP kinase-dependent phosphorylation of synapsin I can contribute to both the chronic and acute actions of neurotrophins in the central nervous system.

The observation that sites 4, 5, and 6 undergo $Ca^{2+}$-dependent dephosphorylation upon depolarization, presumably mediated by protein phosphatase 2K (calcineurin), is of interest. Based on this observation, presynaptic entry of $Ca^{2+}$ could have opposing effects on the phosphorylation at sites 1, 2, and 3, while decreasing phosphorylation at sites 4, 5, and 6. This, in turn, would be expected to have opposing effects on synapsin I-actin interactions. It has been found that neurotrophins are able to enhance phosphorylation of synapsin I at MAP kinase-dependent sites. Since BDNF and neurotrophin-3 have been reported to elevate intracellular $Ca^{2+}$ in hippocampal neurons, and since $Ca^{2+}$ can decrease the phosphorylation state of synapsin I at sites 4, 5, and 6, it is possible that neurotrophins exert bi-directional control of the phosphorylation of synapsin I at these sites. Further work will determine the contribution that $Ca^{2+}$-regulated activation of MAP kinase plays in the regulation of synapsin I phosphorylation by neurotrophins.

What is claimed is:

1. A method for increasing synapsin phosphorylation in neuronal cells comprising exposing said neuronal cells to a pharmaceutical composition consisting of an effective synapsin phosphorylation increasing amount of interleukin-6 IL-6) and a pharmaceutical carrier or excipient.

2. The method of claim 1 wherein said synapsin in said neuronal cells is selected from the group consisting of synapsin I and synapsin II.

3. The method of claim 1 wherein said interleukin-6 (IL-6) promotes the MAP kinase-dependent phosphorylation of said synapsin.

4. The method of claim 1 wherein said neuronal cells are present in a mammalian nervous system.

5. The method of claim 4 wherein said mammalian nervous system is a human nervous system.

6. The method of claim 5 wherein said neuronal cells are degenerating in a patient with Alzheimer's disease.

7. The method of claim 4 wherein said neuronal cells are degenerating.

8. A method for increasing synapsin-mediated neurotransmitter release in neuronal cells through synapsin phosphorylation comprising exposing said neuronal cells to a pharmaceutical composition consisting of an effective synapsin phosphorylation increasing amount of interleukin-6 (IL-6) and a pharmaceutical carrier or excipient.

9. The method of claim 8 wherein said synapsin in said neuronal cells is selected from the group consisting of synapsin I and synapsin II.

10. The method of claim 8 wherein said interleukin-6 (IL-6) promotes the MAP kinase-dependent phosphorylation of said synapsin.

11. The method of claim 8 wherein said neuronal cells are present in a mammalian nervous system.

12. The method of claim 11 wherein said mammalian nervous system is a human nervous system.

13. The method of claim 12 wherein said neuronal cells are degenerating in a patient with Alzheimer's disease.

14. The method of claim 11 wherein said neuronal cells are degenerating.

* * * * *

UNITED STATES PATENT AND TRADEMARK OFFICE
CERTIFICATE OF CORRECTION

PATENT NO.    : 6,444,201 B1
DATED         : September 3, 2002
INVENTOR(S)   : Hui-Quan Han et al.

Page 1 of 1

It is certified that error appears in the above-identified patent and that said Letters Patent is hereby corrected as shown below:

<u>Title page,</u>
Item [73], Assignees: the name of the second Assignee should read: -- Brigham and Women's Hospital, Boston, MA -- instead of: "Brighan and Women's Hospital, Boston, MA"

Signed and Sealed this

Twenty-fifth Day of March, 2003

JAMES E. ROGAN
*Director of the United States Patent and Trademark Office*